United States Patent
Kato et al.

[11] Patent Number: 5,910,485
[45] Date of Patent: Jun. 8, 1999

[54] ANTITUMOR AGENTS COMPRISING AS THE PRINCIPAL COMPOUNDS CONTAINING SILICON AND NITROGEN

[75] Inventors: Masao Kato, Tsukuba; Kazunori Kataoka, Kashiwa; Yukio Nagasaki, Ibaraki; Tsutomu Takezawa, Koshigaya, all of Japan

[73] Assignee: Japan Science and Technology Corporation, Kawaguchi, Japan

[21] Appl. No.: 08/913,219
[22] PCT Filed: Jan. 29, 1997
[86] PCT No.: PCT/JP97/00200
  § 371 Date: Sep. 10, 1997
  § 102(e) Date: Sep. 10, 1997
[87] PCT Pub. No.: WO97/27859
  PCT Pub. Date: Aug. 7, 1997

[30] Foreign Application Priority Data

Jan. 31, 1996 [JP] Japan ................................ 8-015484

[51] Int. Cl.$^6$ .................... A61K 31/70; A61K 31/695
[52] U.S. Cl. ................................... 514/34; 514/63
[58] Field of Search ............................ 514/63, 34

[56] References Cited

U.S. PATENT DOCUMENTS 5,646,124 7/1997 Prakash et al. .

FOREIGN PATENT DOCUMENTS

| 4275233 | 9/1992 | Japan . |
| 827004 | 1/1996 | Japan . |
| 827159 | 1/1996 | Japan . |

OTHER PUBLICATIONS

Carter et al., Chemotherapy of Cancer, second edition, Wiley & Sons, NY ,NY, p. 90–1, 1981.
Wong, et al., Med. Sci. Res., 1989, vol. 17, No. 3, pp. 167–169.

Primary Examiner—Jerome D. Goldberg
Attorney, Agent, or Firm—Sherman and Shalloway

[57] ABSTRACT

Antitumor agent which comprises as the principal agent a mixture of organic compounds having amino group and silyl group (reffered to as silamines) and represented by structural formulae with Adriamycin. Use of silamines in the form of a mixture with Adriamycin, which is an anti-cancer agent showing a potent effect but having extremely serious side effects, makes it possible to highly potentiate the anti-cancer properties of Adriamycin. As a result, the dose of Adriamycincan be reduced and thus its side effects can be relatively relieved as compared with the case where it is used alone.

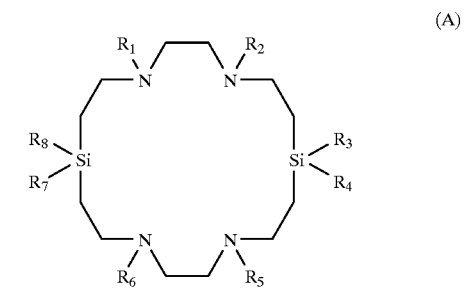

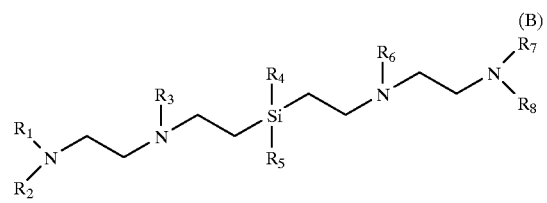

[wherein $R_1$, $R_2$, $R_3$, $R_4$, $R_5$, $R_6$, $R_7$ and $R_8$ represent each hydrogen or $C_{1-10}$ alkyl, aryl or aralkyl, or the pair of $R_1$ with $R_2$ and that of $R_5$ with $R_6$ may be bonded via alkylene, allylene or aralkylene.]

9 Claims, 2 Drawing Sheets

ANTITUMOR AGENTS COMPRISING AS THE PRINCIPAL COMPOUNDS CONTAINING SILICON AND NITROGEN

CROSS-REFERENCE TO RELATED APPLICATION

This is the National Phase application based on International Application PCT/JP97/00200 filed Jan. 29, 1997 and published on Aug. 7, 1997 under number WO 97/27859.

FIELD OF THE INVENTION

This invention relates to an antitumor agent whose principal ingredient is a mixture of an organic compound which contains an amino group and a silyl group, and Adriamycin.

BACKGROUND OF THE INVENTION

The conventional antitumor agents in chemotherapy are mainly classified into a group of antibiotics (for instance Adriamycin) and a group of antimetabolites (for instance 5-fluorouracil). Each group relatively has a feature of a concentration dependence drug and a time dependence drug, and both groups have a problem of being toxic to normal cells. Recently, along with the progress of surgical treatment techniques, expectations for chemotherapy, especially for an antitumor agent whose side effects are minimized, are increasing.

Strong physiological activity of organic silicon compounds has been found by Voronkov et al of Russia (silatrane), and have been investigated in detail. However, sometimes some kinds of silatrane are strongly toxic in accordance with species of substitution group, and some of them have more strong toxicity than hydrocyanamic acid or strychnine. Recently, a group comprised of Shin-etsu Chemical Products Co., Ltd, and Keio University have investigated antineoplastic features of various kinds of organic silicon compounds, and have proceeded with development of relatively low toxicity and high activaty antitumor agents (Chemical Society of Japan, 1990, No. 5, 566–574).

Inventors of this invention have already developed new antitumor agents of ring and chain compounds including silicon and nitrogen (hereafter; shortened to silamine compounds) by investigating thoroughly the antitumor features of silamine compounds (Japanese Patent Application 157518/94 and 157519/94).

However, although the toxicity of these silamine compounds are weaker than that of the antitumor agents such as Adriamycin, its antitumor activity is about $\frac{1}{10}$, and said lower antitumor activity is pointed out as a problem.

The object of this invention is to solve the above mentioned problem of silamine compounds, and to provide a new antitumor agent of lower toxicity and high effectiveness.

DISCLOSURE OF THE INVENTION

The important point of this invention is an antitumor agent which comprises a mixture of a compound having the following chemical formula (A) and Adriamycin,

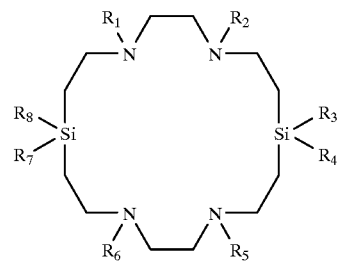

[wherein $R_1$, $R_2$, $R_3$, $R_4$, $R_5$, $R_6$, $R_7$, and $R_8$ represent hydrogen atom, or alkyl group, allyl group or aralkyl group of carbon number 1 to 10; further, a pair of $R_1$ and $R_2$, and a pair of $R_5$ and $R_6$ can be chemically bonded via alkylene, allylene or aralkylene group] and an antitumor agent which comprises a mixture of a compound indicated by following chemical formula (B) and Adriamycin,

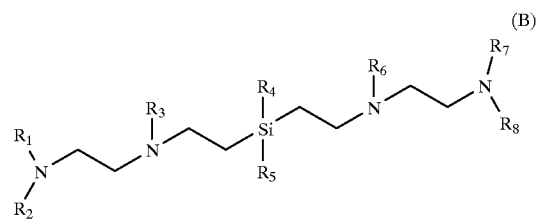

[wherein $R_1$, $R_2$, $R_3$, $R_4$, $R_5$, $R_6$, $R_7$ and $R_8$ represent hydrogen atom, or alkyl group, allyl group or aralkyl group of carbon number 1 to 10; further, a pair of $R_1$ and $R_3$, and a pair of $R_6$ and $R_7$ can be chemically bonded via alkylene, allylene or aralkylene group].

That is, in this invention, by combining Adriamycin which is an antitumor agent classified into conventional antibiotics with silamine compounds, those antitumor features act synergistically, and as the result, the toxicity which is a feature of Adriamycin can be relatively weakened. Adriamycin, as noted in The Merck Index, Eleventh Edition (1989), was formerly the generic name for Doxorubicin, and is (8S-cis)-10-[(3-amino-2,3,6-trideoxy)-α-L-lyxo-hexopyranosyl)oxy]-7,8,9,10-tetrahydro-6,8,11-trihydroxy-8-(hydroxyacetyl)-1-methoxy-5,12-naphthacenedione.

As the compound indicated by chemical formula (A) of this invention, following compounds can be mentioned. 4,7,13,16-tetraethyl-1,1,10,10-tetramethyl-4,7,13,16-tetraaza-1,10-disilacyclooctadecane, 1,1,4,7,10,10,13,16-octamethyl-4,7,13,16-tetraaza-1,10-disilacyclooctadecane, 1,1,4,7,10,10,13,16-octamethyl-4,7,13,16-tetraaza-1,10-disilacyclooctadecane and others.

Compound (A) can be obtained by the method disclosed in our previous document, Japanese Patent Application 157518/94.

That is, it can be synthesized using alkali metal compound, e.g. buthyllithium, as a catalyst, by a reaction of vinylsilane compound indicated by general formula (X) with N,N' substituted ethylenediamine derivatives indicated by general formula (Y).

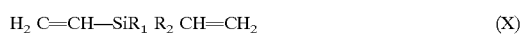

[wherein $R_1$ and $R_2$ is have the same meaning as given above].

[wherein $R_1$ and $R_2$ have the same meaning as given above].

As the reacting mechanism, it is considered that vinylsilane compound reacts with ethylenediamine derivative as a first step, then a cyclization reaction occurs, and this is considered to be so called two step cyclic addition reaction. Chemical reaction formula is indicated as follows.

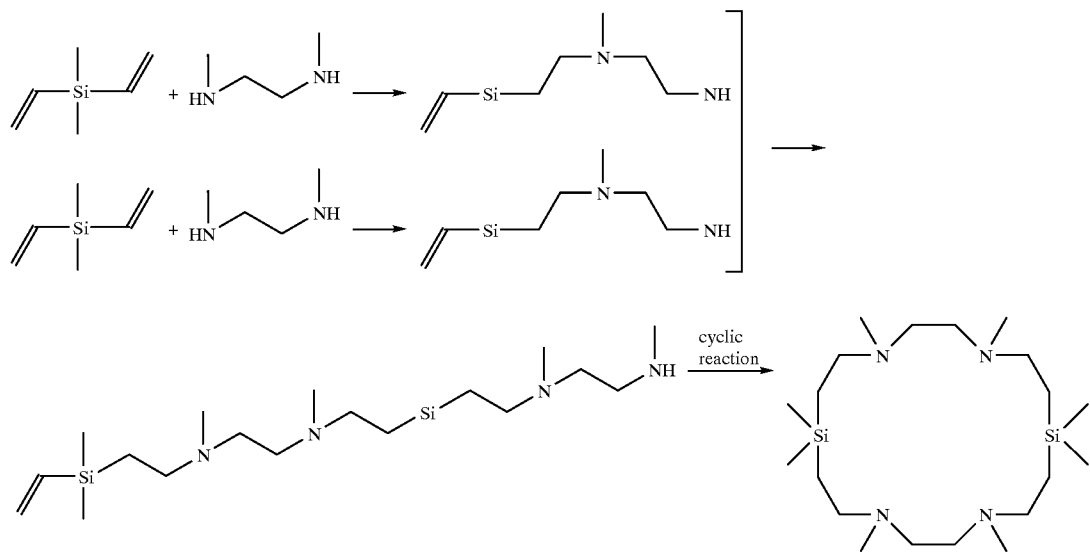

As the compound indicated by chemical formula (B) of this invention, following compounds can be mentioned; 3,6,12,15-tetraethyl-9,9-dimethyl-3,6,12,15-tetraaza-9-silaheptadecane, 6,12-diethyl-9,9'-dimethyl-3,6,12,15-tetraaza-9-silaheptadecane, 4,7,7,10-tetramethyl-1,4,10,13-tetraaza-7-silatridecane,4,10-diethyl-7,7-dimethyl-1,4,10,13-tetraaza-7-silatridecane, and others.

These compounds can be obtained by the above mentioned manufacturing method disclosed in Japanese Patent Application 157518/94.

That is, it can be synthesized by an addition reaction of bis($\alpha,\beta$-unsaturated)silane derivatives and amine using alkali metal compound as a catalyst. This reaction is desirably carried out in the presence of alkali metal compound, and the preparing method of this alkali metal catalyst is strictly restricted. It can be obtained by a reaction between amine to be used and a specific organic alkali metal. As an organic alkali metal to be used, bulky lithiumamide, sodiumamide and potassiumamide represented by lithiumdiisopropylamide, alkyl and allyl lithium such as buthyllithium or diphenyllithium and aralkyllithium can be mentioned. Further, lithium hydride, sodium hydride and potassium hydride can be used.

Molar ratio of alkali metal compound to amine is possible to be from 1/100 to 100/1, and desirable region is from 1/10 to 3/1.

This reaction can be carried out in the presence of inert solvent. As a solvent, liquid which does not react with alkali metal amide catalyst under the reaction conditions can be used. Concretely, ethers such as diethylether, dioxane, tetrahydrofuran, dimethoxyethane or diglyme, aliphatic hydrocarbon such as pentane, hexane, cyclohexane or octane, dimethyl sulfoxide, aromatic hydrocarbon such as benzene or toluene, non-proton polar solvent such as N,N-dimethylformamide or hexamethylphosphorictriamide can be mentioned. In these solvents, ethers such as tetrahydrofuran, aromatic hydrocarbons such as benzene and aliphatic hydrocarbon such as hexane are preferably used.

Volume of solvent to be used in this invention is desirably to be from 1/10 to 50 times to the volume of bis ($\alpha,\beta$-unsaturated)silane derivatives and more desirably from 1/2 to 20 times. In general, when quantity of solvent relatively increases, reaction velocity becomes slow.

Reaction temperature is not restricted, however, a desirable temperature region is from $-78°$ C. to $150°$ C. and more desirable region is $0°$ C. to $80°$ C. And also reacting period is not restricted, however, a desirable reaction period is from 1 minute to 1000 hours, and more desirably from 10 minutes to 100 hours.

The ring or chain silamine compound (hereafter shortened to silamine compound) is mixed together with Adriamycin, and the mixture is evaluated as an antitumor agent. The mixing ratio of silamine compound is desirably from 0.01 to 500 parts to 1 part of Adriamycin by weight, and more desirably from 0.1 to 50 parts by weight.

At the mixing procedure of a silamine compound and Adriamycin, it is possible to use a solvent. As a solvent to be used, a buffer solution such as phosphoric acid buffer or HEPES buffer can be used as well as water. Further, for the improvement of dissolving feature of silamine compounds, it is possible to add ethanol to the solution. Solvent can be added by voluntary quantity, however, preferable quantity is from 0.1 to 500 parts to 1 part of silamine by weight.

An aqueous solution of mixture of silamine/Adriamycin is sterilized, then administered to tumor. As a sterilization method, any known method can be used, however, a sterilization by an autoclave or a filtration by 0.22 μm syringe filter is recommendable because of its easy handling. A dosage of medicine is respectively altered according to the size of tumor. Desirable dosage of Adriamycin is from 0.01 to 100 mg/kg and for silamine compound is from 0.1 to 1000 mg/kg, further, the most desirable dosage for Adriamycin is from 0.1 to 10 mg/kg and for silamine compound is from 1 to 200 mg/kg. The mixture can be administered by a hypodermic injection, an abdominal injection, an intravenous injection or an artery injection, or by an oral dosage form.

THE BEST EMBODIMENT TO CARRY OUT THE INVENTION

The present invention will be understood more readily with reference to the following Examples, however these Examples are intended to illustrate the invention in detail and are not to be construed to limit the scope of the invention.

EXAMPLE 1

Figure 1:
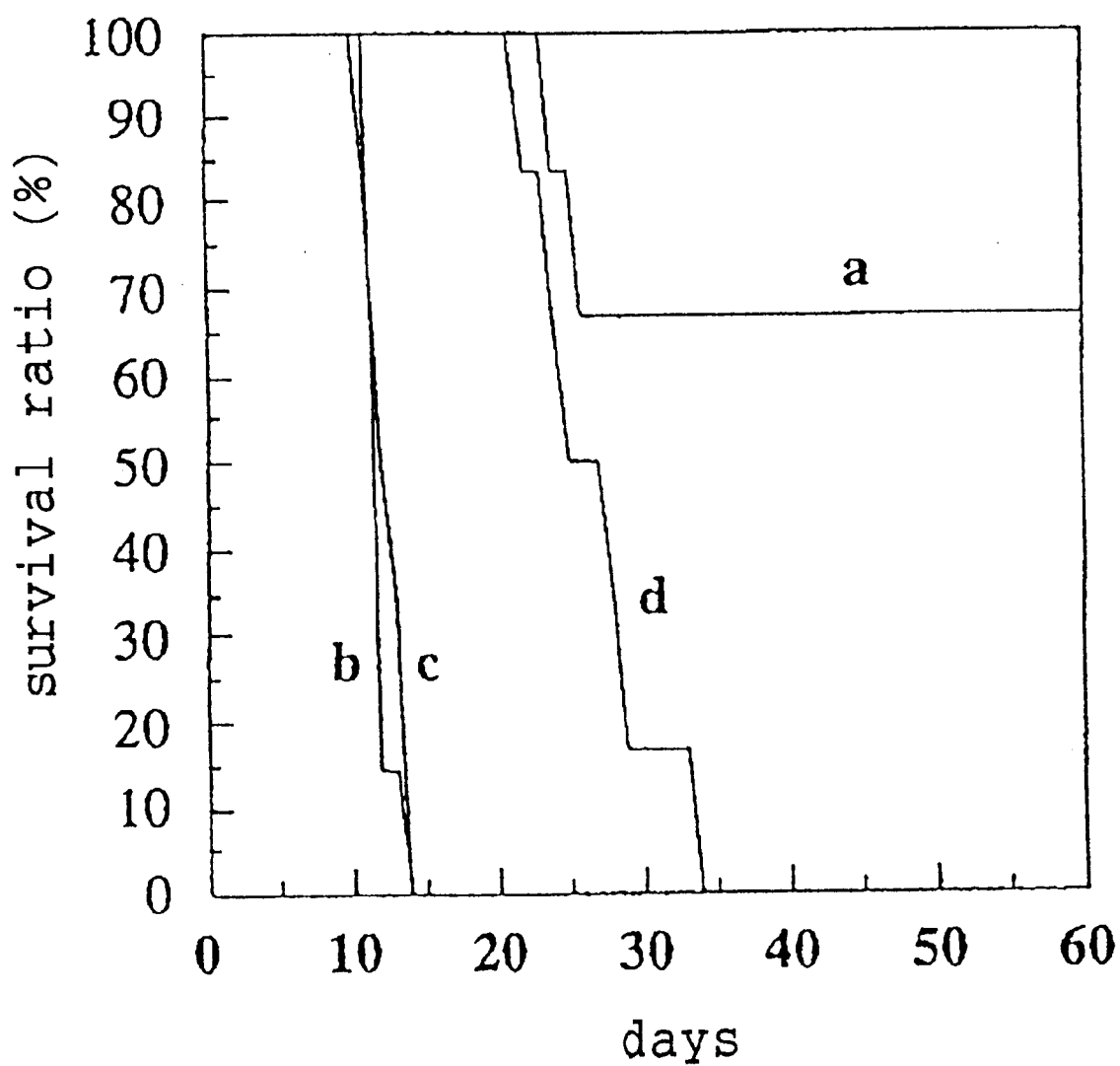
FIG. 1 shows a survival variation curve per days of test mice (wherein, a: compound C 50 mg/kg+Adriamycin 4 mg/kg; b: phosphoric acid buffer solution 0.1 ml/10 g; c: compound C 50 mg/kg; d: Adriamycin 4 mg/kg; prescribed for 3 times . . . 1st, 5th and 9th day).
Figure 2:
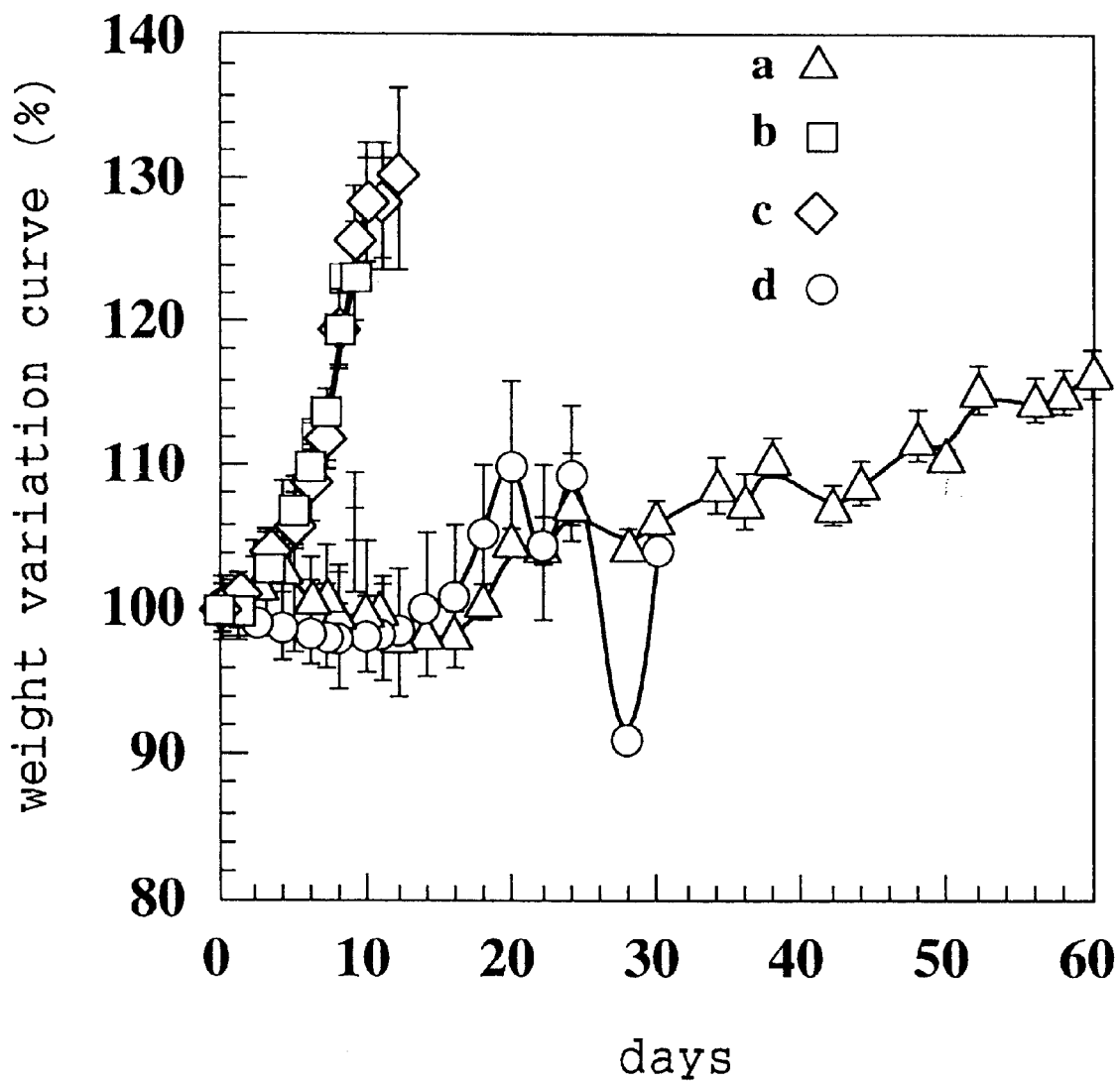
FIG. 2 shows a weight variation curve of mice which are prescribed silamine compounds and Adriamycin (wherein, a: compound C 50 mg/kg+Adriamycin 4 mg/kg; b: phosphoric acid buffer solution 0.1 ml/10 g; c: compound C 50 mg/kg; d: Adriamycin 4 mg/kg; prescribed for 3 times . . . 1st, 5th and 9th day).

First, $1.0 \times 10^6$ cells of P388 mouse leukemia cell are prescribed to six CDF1(♀) mice, and mice with cancer are prepared. After 1, 5 and 9 days, a mixture of 4,7,13,16-tetraethyl-1,1,10,10-tetramethyl-4,7,13,16-tetraaza-1,10-disilacyclooctadecane indicated by following chemical formula (C) and Adriamycin (respective prescribing amount is 50 mg/kg and 4 mg/kg) is injected into the abdominal cavity of each mouse. One mouse died at 25th day and another one mouse died at 27th day, and other four mice survived for 60 days. The relationship between the number of days of prescribing and the survival ratio of mice is shown in FIG. 1 (curve a). Further, the relationship between the number of days of prescribing and the weight reduction of mice in comparison with comparison groups (b, c and d) which will be mentioned later, are shown in FIG. 2 (see curve a). From the results of FIG. 2 (curve a), the weight reduction of mice is smaller compared with that of the comparison groups (curves b, c and d).

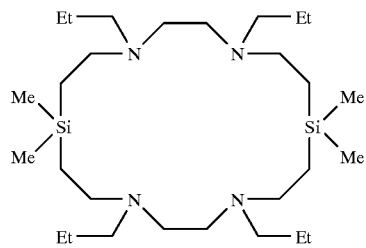

(C)

Referential Example 1

Mice with cancer are prepared similarly to Example 1, and after 1, 5 and 9 days 0.1 ml/10 g of phosphoric acid buffer solution (pH=7.4; ion intensity=0.1) is injected into the abdominal cavity of each mouse. Five mice died at 12th day and another one mouse died at 14th day. The relationship between the number of days of prescribing and the survival ratio of mice is shown in FIG. 1 (curve b).

Referential Example 2

Mice with cancer are prepared similarly to Example 1, and after 1, 5 and 9 days 50 mg of compound C is injected into the abdominal cavity of each mouse. One mouse died at 11th day, two mice died at 12th day and two mice died at 13th day. The relationship between the number of days of prescribing and the survival ratio of mice is shown in FIG. 1 (curve c).

Referential Example 3

Mice with cancer are prepared similarly to Example 1, and after 1, 5 and 9 days 4 mg of Adriamycin is injected into the abdominal cavity of each mouse. One mouse died at 23rd day, two mice died at 25th day and 28th day, and one mouse died at 34th day. The relationship between the number of days of prescribing and the survival ratio of mice is shown in FIG. 1 (curve d).

The weight reduction curve of mice after the prescribing of Adriamycin alone is shown in curve d FIG. 2. It is understood from this figure that the weight reduction after Adriamycin prescribing is bigger than that seen in Example 1.

EXAMPLE 2

$1.0 \times 10^6$ cells of P388 mouse leukemia cell are prescribed to six CDF1(♀) mice, and mice with cancer are prepared. After 1, 5 and 9 days, a mixture of compound (C) and Adriamycin (respective injecting amount is 50 mg/kg and 4 mg/kg) is injected into the abdominal cavity of each mouse. Further, 50 mg/kg of compound (C) is injected into the abdominal cavity of each mice at 2nd, 3rd, 4th, 6th, 7th and 8th day. After 60 days all six mice are surviving.

Referential Example 4

Mice with cancer are prepared similarly to Example 2, and 0.1 ml/10 g of phosphoric acid buffer solution (pH=7.4; ion intensity=0.1) is injected into the abdominal cavity of each mouse at every day from 1st to 9th day. Five mice died at 12th day and another one mouse died at 13th day.

Referential Example 5

Mice with cancer are prepared smilarly to Example 1, and 50 mg/kg of compound (D) is injected at every day from 1st to 9th day into the abdominal cavity of each mouse. One mouse died at 14th day, two mice died at 15th day, one mouse died at 17th day and two mice died at 18th day.

EXAMPLE 3

$1.0 \times 10^6$ cells of P388 mouse leukemia cell is prescribed to six CDF1(♀) mice, and mice with cancer are prepared. After 1, 5 and 9 days, a mixture of 3,6,12,15-tetraethyl-9,9-dimethyl-3,6,12,15-tetraaza-9-silaheptadecane indicated by following chemical formula (D) and Adriamycin are injected (respective injection amount is 50 mg/kg and 4 mg/kg) into the abdominal cavity of each mouse. One mouse died at 23rd day, 25th day and 30th day, and other three mice survived for 60 days. The weight reduction of mice is smaller compared with that of comparison groups which will be mentioned later.

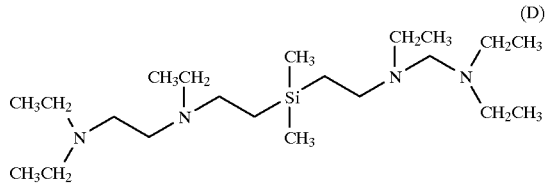

Referential Example 6

Mice with cancer are prepared similarly to Example 1, and after 1, 5 and 9 days 50 mg of compound (D) is injected into an abdominal cavity of each mouse. Two mice died at 11th day, one mouse died at 12th day, two mice died at 13th day and one mouse died at 14th day.

POSSIBILITY FOR PRACTICAL INDUSTRIAL USE

The chain and ring silamine compounds of this invention generate remarkable antitumor feature when it is used together with Adriamycin by voluntary mixing ratio. The use of Adriamycin alone has a problem of strong toxicity, however, since when it is used together with silamine it generates remarkably high activity, toxicity is weakened relatively and it is provided as a new and highly effective antitumor agent.

We claim:

1. A composition which comprises a mixture of a compound represented by the formula (A) and Adriamycin

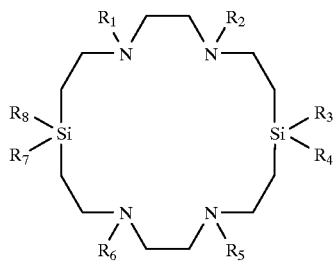

wherein $R_1$, $R_2$, $R_3$, $R_4$, $R_5$, $R_6$, $R_7$, and $R_8$ independently represent hydrogen atom, or alkyl group, allyl group, or aralkyl group of carbon number 1 to 10; and; at a mixing ratio of 0.01 to 500 parts by weight of said compound of formula (A) per 1 part by weight of Adriamycin.

2. The composition of claim 1 wherein said mixing ratio is 0.1 to 50 parts by weight of the compound of formula (A) per 1 part by weight of Adriamycin.

3. The composition of claim 1 wherein the compound of formula (A) is 4,7,13,16-tetraethyl-1,1,10,10-tetramethyl-4,7,13,16-tetraaza-1,10-disilacyclooctadecane, 1,1,4,7,10,10,13,16-octamethyl-4,7,13,16-tetraaza-1,10-disilacyclooctadecane, or 1,1,4,7,10,10,13,16-octamethyl-4,7,13,16-tetraaza-1,10-disilacyclooctadecane.

4. The composition of claim 1 wherein the compound of formula (A) comprises 4,7,13,16-tetraethyl-1,1,10,10-tetramethyl-4,7,13,16-tetraaza-1,10-disilacyclooctadecane.

5. A method for treating a tumor in a patient in need thereof which comprises administering to said patient an antitumor effective amount of a mixture of from 0.1 to 1000 mg/kg body weight of said patient of silamine compound of compound (A) of the formula

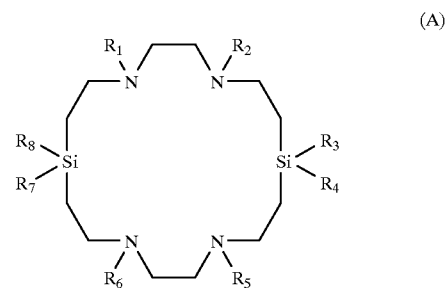

wherein $R^1$, $R^2$, $R^3$, $R^4$, $R^5$, $R^6$, $R^7$ and $R^8$ independently represent hydrogen atom, or alkyl group, or aralkyl group of carbon number 1 to 10; and in formula (B) the pairs $R_1$ and $R_3$ and $R_6$ and $R_7$, may be chemically bonded via alkylene, allylene or aralkylene group; and from 0.01 to 100 mg/kg body weight of said patient of adriamycin wherein the tumor is sensitive to the above mixture.

6. The method of claim 5 wherein the silamine compound and adriamycin are administered to the patient at a weight mixing ratio of from 0.001 to 500 parts of the silamine compound per 1 part by weight of adriamycin.

7. The method of claim 10 wherein the cancerous condition is leukemia.

8. The method of claim 5 wherein the silamine compound and adriamycin are administered to the patient at a weight mixing ratio of from 0.1 to 50 parts of the silamine compound per 1 part by weight of adriamycin.

9. The method of claim 8 wherein from 1 to 200 mg of silamine compound and from 0.1 to 10 mg of adriamycin each per kilogram body weight are administered to the patient.

* * * * *